United States Patent
Nagao et al.

(10) Patent No.: US 8,305,179 B2
(45) Date of Patent: Nov. 6, 2012

(54) OIL IMMERSED ELECTRICAL APPARATUS

(75) Inventors: Eiichi Nagao, Chiyoda-ku (JP); Kentaro Taninouchi, Chiyoda-ku (JP); Noboru Hosokawa, Chiyoda-ku (JP); Tsuyoshi Amimoto, Chiyoda-ku (JP); Kozo Tachibana, Chiyoda-ku (JP); Takanori Sone, Chiyoda-ku (JP); Junji Tanimura, Chiyoda-ku (JP); Satoru Toyama, Chiyoda-ku (JP)

(73) Assignee: Mitsubishi Electric Corporation, Chiyoda-Ku, Tokyo (JP)

( * ) Notice: Subject to any disclaimer, the term of this patent is extended or adjusted under 35 U.S.C. 154(b) by 15 days.

(21) Appl. No.: 12/999,919

(22) PCT Filed: Sep. 26, 2008

(86) PCT No.: PCT/JP2008/067536
§ 371 (c)(1),
(2), (4) Date: Dec. 17, 2010

(87) PCT Pub. No.: WO2010/035336
PCT Pub. Date: Apr. 1, 2010

(65) Prior Publication Data
US 2011/0090034 A1    Apr. 21, 2011

(51) Int. Cl.
*H01F 27/10*    (2006.01)
*H01H 31/12*    (2006.01)
(52) U.S. Cl. ............................ 336/58; 324/551; 324/541
(58) Field of Classification Search .................... 336/55, 336/58, 61; 324/126, 509, 533, 537, 536, 324/544, 551, 555
See application file for complete search history.

(56) References Cited

U.S. PATENT DOCUMENTS

| 1,776,309 | A | * | 9/1930 | Clark | 174/14 R |
| 2,750,562 | A | * | 6/1956 | Starr | 324/528 |
| 3,466,378 | A | * | 9/1969 | Mathes | 174/15.4 |
| 3,753,087 | A | * | 8/1973 | Tan | 324/523 |
| 3,862,491 | A | * | 1/1975 | Richardson | 29/593 |

(Continued)

FOREIGN PATENT DOCUMENTS
JP    40-021724 B1    9/1965
(Continued)

OTHER PUBLICATIONS
International Search Report (PCT/ISA/210) for PCT/JP2009/067536 dated Dec. 22, 2008.
(Continued)

*Primary Examiner* — Mohamad Musleh
*Assistant Examiner* — Joselito Baisa
(74) *Attorney, Agent, or Firm* — Buchanan Ingersoll & Rooney PC

(57) ABSTRACT

An oil immersed electrical apparatus such as an oil immersed transformer that can detect copper sulfide precipitated on coil insulating paper is provided. In the oil immersed transformer in which a coil with its surface covered by insulating paper is arranged in a container filled with insulating oil, a detection member is prepared by providing two electrodes on a surface of a plate-like pressboard formed of cellulose, which is a same material as that of the insulating paper, this detection member is arranged in contact with the insulating oil, and generation of copper sulfide is detected from reduction in a surface resistance between the electrodes. The temperature of the detection member is set higher than the temperature of the coil so that copper sulfide is generated thereon prior to generation of copper sulfide on a coil unit.

20 Claims, 3 Drawing Sheets

U.S. PATENT DOCUMENTS

| | | | |
|---|---|---|---|
| 3,987,260 A * | 10/1976 | Wilson | 218/79 |
| 4,338,561 A * | 7/1982 | Zaengl et al. | 323/208 |
| 4,675,662 A * | 6/1987 | Kondo et al. | 340/631 |
| 4,737,775 A * | 4/1988 | Tokuda et al. | 340/647 |
| 4,833,396 A * | 5/1989 | Haberland | 324/537 |
| 5,117,191 A * | 5/1992 | Saigo et al. | 324/551 |
| 5,414,368 A * | 5/1995 | Ogawa et al. | 324/675 |
| 5,469,066 A * | 11/1995 | Ito et al. | 324/551 |
| 7,129,710 B2 * | 10/2006 | Bager | 324/525 |
| 7,659,728 B1 * | 2/2010 | Watkins, Jr. | 324/551 |
| 2010/0192673 A1 | 8/2010 | Toyama et al. | |

FOREIGN PATENT DOCUMENTS

| | | |
|---|---|---|
| JP | 57-141565 A | 9/1982 |
| JP | 62-103216 U | 7/1987 |
| JP | 4-176108 A | 6/1992 |
| JP | 07-335446 A | 12/1995 |
| JP | 2000-353623 A | 12/2000 |
| JP | 2003289008 A * | 10/2003 |
| WO | WO 2009/054156 A1 | 4/2009 |
| WO | WO 2009/110073 A1 | 9/2009 |

OTHER PUBLICATIONS

Written Opinion (PCT/ISA/237) for PCT/JP2009/067536 dated Dec. 22, 2008.

CIGRE TF A2.31, "Copper Sulphide in Transformer Insulation", ELECTRA, Feb. 2006, pp. 20-23, No. 224.

F. Scatiggio et al., "Corrosive Sulfur in Insulating Oils: Its Detection and Correlated Power Apparatus Failures", IEEE Transactions on Power Delivery, Jan. 2008, pp. 508-509, vol. 23, No. 1.

The Extended Search Report from European Patent Office issued in corresponding European patent application No. 08877073.0, dated Jun. 13, 2012.

* cited by examiner

OIL IMMERSED ELECTRICAL APPARATUS

TECHNICAL FIELD

The present invention relates to an oil immersed electrical apparatus such as an oil immersed transformer.

BACKGROUND ART

In an oil immersed electrical apparatus such as an oil immersed transformer, a coil that serves as a current carrying medium is arranged in an insulating oil. This coil may be a copper coil formed of copper. Insulating paper is wound around the copper coil so that the copper coil would not be short-circuited between adjacent turns.

Meanwhile, the mineral oil (the aforementioned insulating oil) adopted for the oil immersed transformer contains sulfur elements. The sulfur elements react with easily-sulfurized metals such as copper and silver that are used in the oil immersed transformer to produce conductive sulfides. For example, a sulfur element reacts with the copper components provided in the oil to precipitate conductive copper sulfide on the surface of the insulating paper. Then, a conductive path is formed between adjacent turns of the copper coil, which may cause dielectric breakdown (see, for example, Non-patent Document 1).

Apart from the precipitation of copper sulfide on the insulating paper, a phenomenon has been known in which copper sulfide precipitates on the surface of metal. When this happens, as the amount of copper sulfide produced increases, the copper sulfide that peels off from the surface of the metal and floats in the insulating oil may lower the insulating performance of the apparatus. As a method of avoiding such a phenomenon, a detection member may be provided in the apparatus to detect production of copper sulfide on the metal surface (see, for example, Patent Document 1). In this method, a detection member is prepared by spraying copper powder onto the surfaces of an epoxy resin insulating plate to be dispersed and fixed, the formation of copper sulfide is detected when the surface resistance of this detection member decreases, and thus an abnormality in the apparatus can be diagnosed.

Patent Document 1: Japanese Patent Application Laid-open No. 04-176108
Non-patent Document 1: CIGRE TF A2.31, "Copper Sulphide in Transformer Insulation", ELECTRA, No. 224, pp. 20-23, 2006

DISCLOSURE OF INVENTION

Problem to be Solved by the Invention

The diagnosing method indicated in the above Patent Document 1 relates to precipitation of copper sulfide on a metal surface that has been observed since long ago, and thus is intended for a phenomenon that is different from precipitation of copper sulfide on the surface of insulating paper. In addition, with this diagnosing method, an epoxy resin insulating plate that is prepared with a material different from cellulose of the coil insulating paper is adopted, and therefore precipitation of copper sulfide on the coil insulating paper would not be accurately detected.

In addition, according to Patent Document 1, the epoxy resin insulating plate has to be produced with a complicated method in which copper powder is sprayed to be dispersed and fixed. If the fixed copper powder is peeled off from the epoxy resin insulating plate, it becomes metallic foreign matter floating in the insulating oil, which may reduce the insulating performance of the transformer.

Furthermore, if precipitation of copper sulfide occurs first in any portion other than the detection member, an abnormality in the apparatus cannot be detected.

The present invention has been conceived to solve the above problems. Its object is to provide an oil immersed electrical apparatus that can detect an amount of sulfur compound precipitated on an insulating member (e.g., coil insulating paper) that covers a current carrying medium (e.g., coil) included in a main body of the apparatus so that dielectric breakdown between current carrying media such as turns of the coil can be prevented.

Means for Solving Problem

To solve the above problems and achieve the object, an oil immersed electrical apparatus, in which an electrical apparatus main body is housed in a container filled with insulating oil and the electrical apparatus main body includes a current carrying medium whose surface is covered by an insulating member, includes: a solid insulator that is prepared with a same material as the insulating member and has two electrodes on a surface, the solid insulator being adopted as a detection member that is arranged in contact with the insulating oil to detect a change in an insulation resistance between the electrodes.

Effect of the Invention

According to the present invention, changes in insulation resistance between electrodes are detected by use of a detection member, and thus the precipitation level of sulfur compound on an insulating member that is prepared with the same material as a solid insulator can be detected. Hence, insulation degradation between current carrying media in an electronic apparatus can be prevented.

EXPLANATIONS OF LETTERS OR NUMERALS

Figure 1:
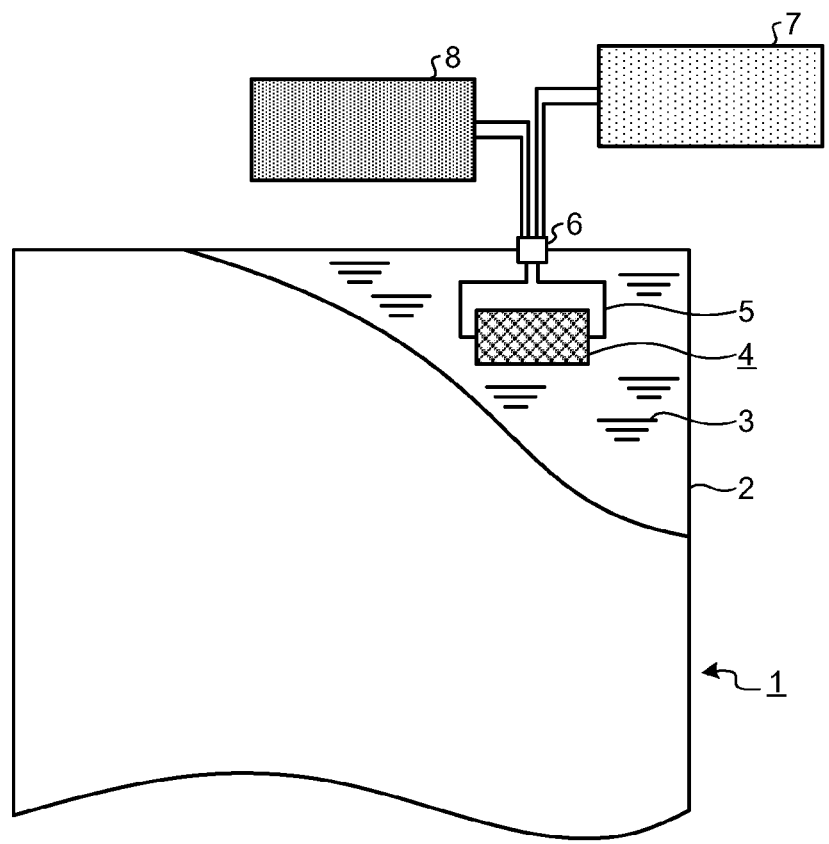
FIG. 1 is a diagram of the structure of an oil immersed transformer according to a first embodiment.

1 Oil immersed transformer
2 Tank
3 Insulating oil
4 Detection member
5 Lead wire
6 Sealing terminal
7 Insulation resistance tester
8 Heater controlling device
11 Pressboard
12 Electrodes
13 Surface resistance measurement lead
14, 18 Heater 15, 19 Heater lead
16 Copper sulfide
17 Insulators

BEST MODE(S) FOR CARRYING OUT THE INVENTION

Exemplary embodiments of the oil immersed electrical apparatus according to the present invention are explained in detail below with reference to the drawings. The invention is not limited by these embodiments.

First Embodiment

An oil immersed electrical apparatus according to an embodiment is explained in detail below by using a transformer as an example. FIG. 1 is a diagram of the structure of an oil immersed transformer according to the present embodiment. As illustrated in FIG. 1, an oil immersed transformer 1 includes a tank 2, insulating oil 3, a detection member 4, a lead wire 5, a sealing terminal 6, an insulation resistance tester 7, and a heater controlling device 8.

The oil immersed transformer 1 has a structure such that a not-shown main body of the electrical apparatus, which includes an iron core and a coil wound around the iron core, is housed in the tank 2, and the tank 2 is filled with the insulating oil 3. The not-shown coil is, for example, a copper coil formed of copper, and insulating paper is wound around the copper coil to avoid a short circuit between adjacent turns. In addition, the detection member 4 is also immersed in the insulating oil 3 to detect formation of sulfide. The detection member 4 is connected to the lead wire 5. This lead wire 5 is drawn out of the tank 2 by way of the sealing terminal 6, and is further connected to the insulation resistance tester 7 and the heater controlling device 8 that are arranged outside the tank 2.

Figure 2:
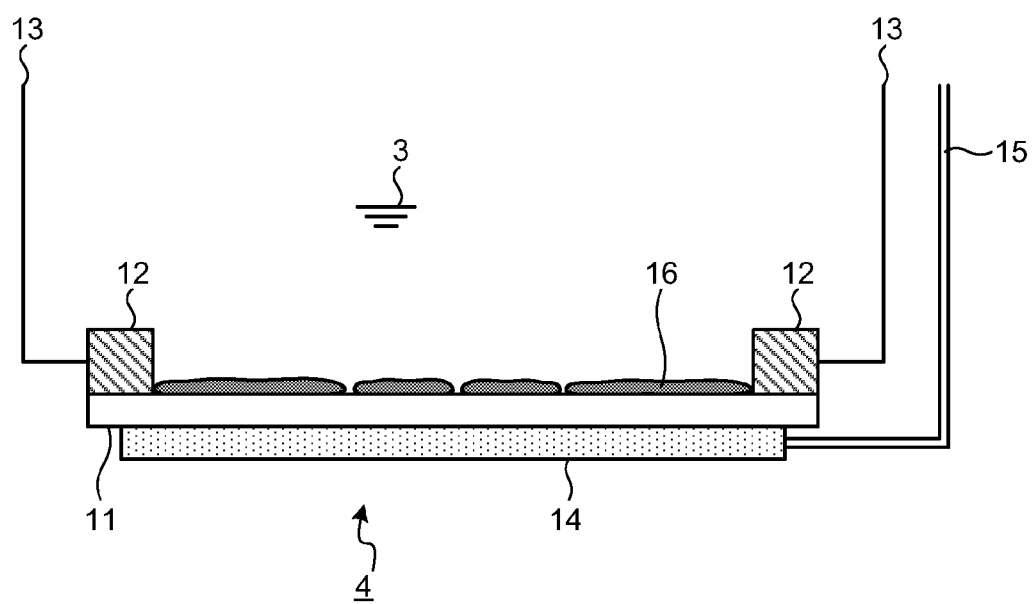
FIG. 2 is a detailed diagram of the structure of a detection member according to the first embodiment.

Next, the detailed structure of the detection member 4 is explained with reference to FIG. 2. FIG. 2 is a detailed diagram of the structure of the detection member 4 according to the first embodiment. As illustrated in FIG. 2, the detection member 4 includes a pressboard 11, electrodes 12, and a surface resistance measurement lead 13. The detection member 4 has a structure that can be heated by a heater 14, and a heater lead 15 is connected to the heater 14. Moreover, copper sulfide 16 is precipitated on the pressboard 11.

The detection member 4 is configured by arranging the two electrodes 12 on one of the surfaces of the pressboard 11 that is a solid insulator shaped into, for example, a plate. The material of the solid insulator that constitutes the pressboard 11 is the same as that of the coil insulating paper, which is cellulose, that serves as an insulating member covering the coil that serves as a current-carrying medium. Furthermore, the two electrodes 12 may be copper electrodes. The two electrodes are positioned at the two ends of the pressboard 11. At least this surface of the pressboard 11 is brought into contact with the insulating oil 3.

The heater 14 is arranged on the other surface of the pressboard 11, and because this surface of the pressboard 11 is brought into contact with the heater 14, the detection member 4 can be heated by the heater 14. The two electrodes 12 are connected to the surface resistance measurement lead 13, and also to the insulation resistance tester 7 illustrated in FIG. 1 by way of this surface resistance measurement lead 13. Moreover, the heater 14 is connected to the heater lead 15, and also to the heater controlling device 8 illustrated in FIG. 1 by way of this heater lead 15. The insulation resistance tester 7 detects the surface resistance between the two electrodes. In addition, the heater controlling device 8 controls heat generation of the heater 14. The lead wire 5 illustrated in FIG. 1 refers to both the surface resistance measurement lead 13 and the heater lead 15 illustrated in FIG. 2.

The mineral oil adopted for the oil immersed transformer 1 contains sulfur elements. It has been known that the sulfur elements react with, for example, copper components in the oil to precipitate conductive copper sulfide on the surface of the insulating paper that covers the not-shown coil. As illustrated in FIG. 2, the copper sulfide 16 precipitated on the surface of the pressboard 11 gradually forms a conductive path between the two electrodes 12, and eventually reduces the resistance between the electrodes (i.e., the surface resistance of the pressboard 11).

According to the present embodiment, because the pressboard 11 is formed by a solid insulator formed of the same material as that of the coil insulating paper, which is cellulose, the precipitation of copper sulfide on the coil insulating paper can be replicated on the pressboard 11.

The copper sulfide 16 is precipitated by reaction between the sulfur elements and the copper components in the mineral oil. In general, the rate of chemical reaction increases as the temperature becomes higher. The same holds for the copper sulfide precipitation, and thus the precipitation becomes more significant at a position of a higher temperature.

Figure 3:
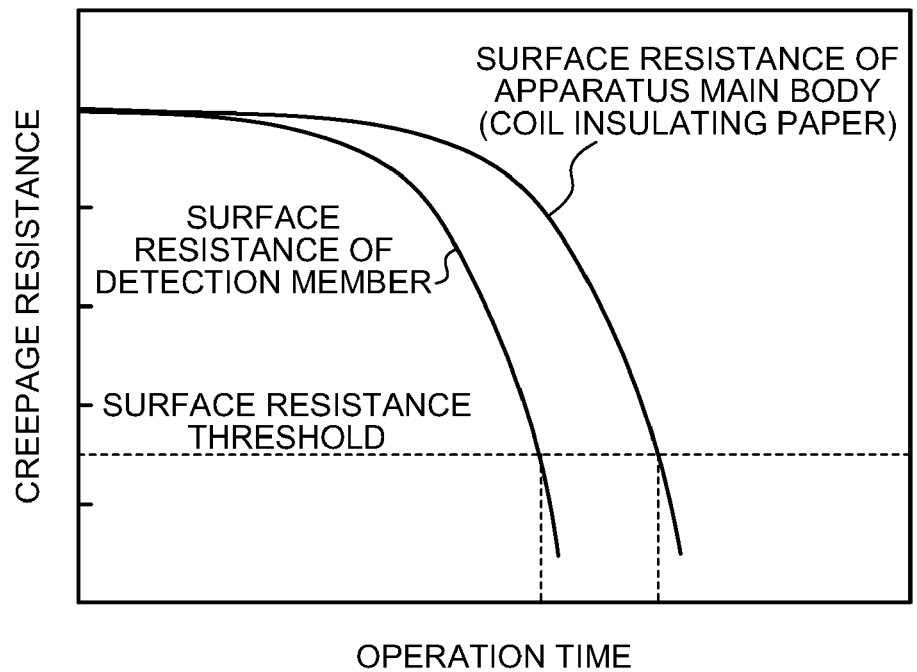
FIG. 3 is a graph illustrating the operation of the detection member.

Next, the operation of the detection member 4 is explained with reference to FIG. 3. FIG. 3 is a graph illustrating the operation of the detection member 4. The horizontal axis represents the operation time of the oil immersed transformer, and the vertical axis represents the creepage resistance (or surface resistance). The threshold value of the surface resistance in FIG. 3 is a value that indicates insufficient insulation if the surface resistance of the coil insulating paper becomes equal to or lower than this value. The value is $1 \times 10^7 \Omega/€$ to $1 \times 10^9 \Omega/€$, which is several orders smaller than the surface resistance of the coil insulating paper on which no copper sulfide 16 is precipitated, i.e., $1 \times 10^{14} \Omega/€$ or greater. Thus, changes in the surface resistance can be easily recognized.

The detection member 4 is heated by the heater 14, and is set at a higher temperature than a coil unit that is the current carrying medium of the main body of the apparatus. The copper sulfide 16 is precipitated first at a position of a higher temperature in the apparatus because of its dependence on temperature in the precipitation reaction. By setting the temperature of the detection member 4 higher than that of the coil unit, the copper sulfide 16 can be precipitated on the detection member 4 before the copper sulfide 16 is precipitated on the coil unit. The surface resistance of the detection member 4 is therefore lowered before the insulating performance of the coil unit is lowered by the precipitation of the copper sulfide 16. For this reason, an abnormality in the apparatus can be prevented. In FIG. 3, change in the surface resistance of the detection member 4 and change in the surface resistance of the apparatus main body (i.e., the coil insulating paper) are indicated. The surface resistance of the detection member 4 falls below the threshold value earlier than the surface resistance of the apparatus main body (i.e., the coil insulating paper) because the detection member 4 is heated by the heater 14.

The insulating oil 3 also functions as a cooling medium for the coil. As it flows through the coil, the temperature of the oil increases, and becomes higher around the top surface of the transformer than the bottom surface. Thus, by arranging the detection member 4 in the upper portion inside the tank 2, the copper sulfide 16 can be precipitated on the detection member 4 earlier than on the coil unit. Then, less heating of the heater 14 is required, and therefore the power consumption can be reduced.

Figure 4:
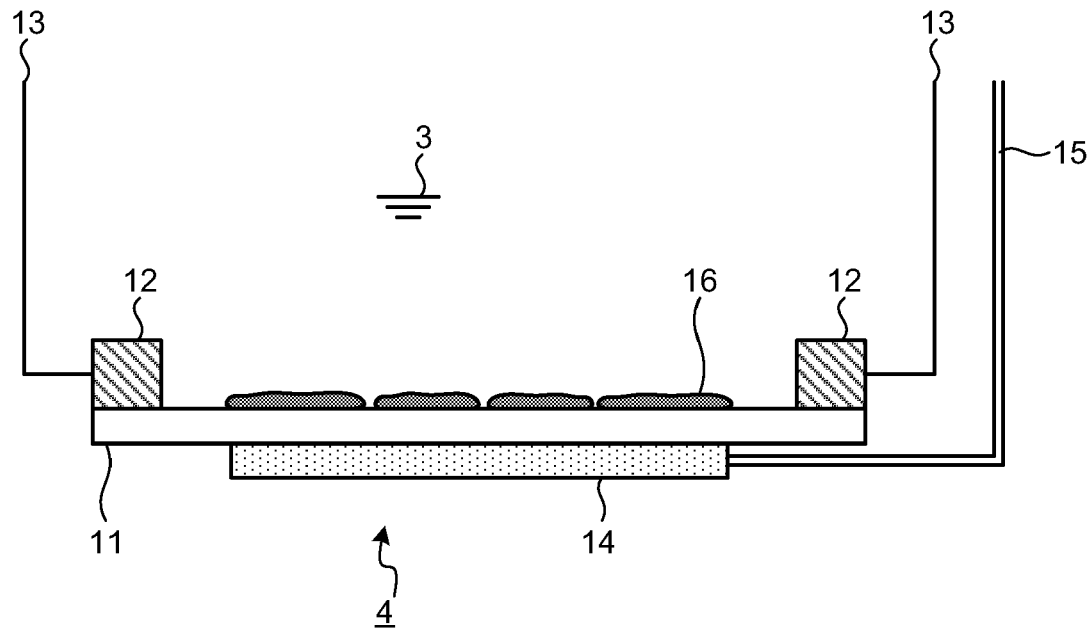
FIG. 4 is a diagram explaining determination of the length of a heater according to the first embodiment.

FIG. 4 is a diagram explaining the length of the heater 14. In this drawing, the length of the heater 14 is smaller than the distance between the two electrodes 12. In such a case, because only the center portion between the two electrodes 12 is heated, the copper sulfide 16 would be precipitated in the center portion of the pressboard 11. However, no conductive path would be created between the two electrodes 12, or it would take longer to crate such a path. Thus, a dielectric breakdown of the coil unit may not be detected in advance. For this reason, the length of the heater 14 (i.e., heating range) is preferably greater than the distance between the two electrodes 12 in order to prevent insufficient insulation of the coil unit.

According to the present embodiment, the surface resistance between the electrodes 12 (insulation resistance) is detected by using the same material (cellulose) as the coil insulating paper for the pressboard 11 included in the detection member 4, and thus precipitation of copper sulfide on the coil insulating paper can be replicated on the pressboard 11. Then, reduction in the surface resistance between the electrodes 12 is detected so that insufficient insulation between turns of the coil can be prevented. In other words, the insufficient insulation of the coil unit can be detected at a stage prior to the surface resistance between the electrodes 12 falling below the threshold value.

In addition, by heating the detection member 4 with the heater 14, the pressboard 11 can be set at a higher temperature than the coil unit, and thus the copper sulfide 16 can be precipitated on the detection member 4 before the copper sulfide 16 is precipitated on the coil unit. As a result, an abnormality in the apparatus can be reliably prevented by detecting reduction in the surface resistance of the detection member 4.

Furthermore, because the insulating oil 3 functions also as a coil cooling medium, the temperature of the oil is higher around the top surface of the transformer than around the bottom surface. Thus, by arranging the detection member 4 in the upper portion of the tank 2, the temperature of the detection member 4 can be easily maintained higher than that of the coil unit, which can reduce the power consumption of the heater 14.

In addition, the length of the heater 14 (heating range) is designed to include the two electrodes 12 and be greater than the distance between the two electrodes 12. By such design, the insulation breakdown of the coil unit can be reliably detected in advance.

Moreover, the electrodes 12 are arranged on one of the surfaces of the plate-like pressboard 11 to use as a precipitation surface for the copper sulfide 16, while the heater 14 is brought into contact with the other surface. Thus, the structure can be simplified.

According to the present embodiment, the detection member 4 is designed to have the electrodes 12 on the plate-like pressboard 11, but the electrodes 12 may be arranged on a solid insulator of a different shape.

Furthermore, in the explanation of the present embodiment, the oil immersed transformer is used as an example, and copper sulfide precipitated on the insulating paper of the coil is detected. However, the embodiment is not limited thereto. Precipitation of sulfide on an insulating member that covers a current carrying medium in the oil immersed electrical apparatus may be detected by a detection member incorporating a solid insulator prepared with the same material as the insulating member.

Second Embodiment

Figure 5:
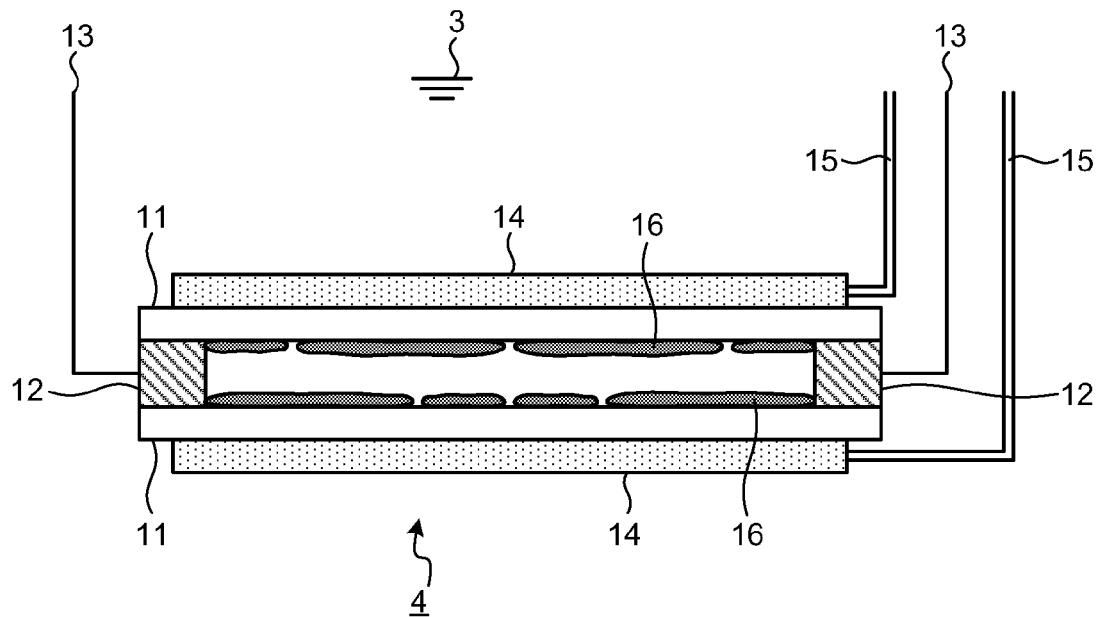
FIG. 5 is a detailed diagram of the structure of a detection member according to a second embodiment.

FIG. 5 is a diagram of the detailed structure of a detection member according to a second embodiment. The structural components that are the same as those of FIG. 1 are given the same reference numerals. The structure according to this embodiment is such that the electrodes 12 are sandwiched by two pressboards 11 to offer a more reliable detection member 4. In particular, in FIG. 5, two plate-like pressboards 11 are positioned parallel to and opposed to each other, and the two electrodes 12 are interposed between these two pressboards 11. Heaters 14 are arranged in contact with the pressboards 11 on the surfaces of the pressboards 11 that are not the surfaces facing each other. The two pressboards 11 are set at the same temperature by the heaters 14. This temperature is set higher than the temperature of the coil unit. In the detection member 4, the two pressboards 11 share the electrodes 12. The properties of the pressboards 11 as solid insulators are the same as the first embodiment.

For example, if foreign matters from the insulating member floating in the insulating oil 3 are stuck onto the pressboard 11, or if the surface of the pressboard 11 is soiled by sebum or the like, precipitation of the copper sulfide 16 may be hindered. Even when such a situation occurs, the reliability can be improved because of the multiple surface resistance detection surfaces (two surfaces in the illustrated example) according to the embodiment.

According to the present embodiment, the two pressboards 11 are arranged opposed to each other to use the opposing surfaces as surface resistance detection surfaces. Other arrangements may be adopted, and the number of detection surfaces is not limited to two. However, with the arrangement as indicated in the present embodiment, the structure of the detection member 4 can be made compact.

Third Embodiment

Figure 6:
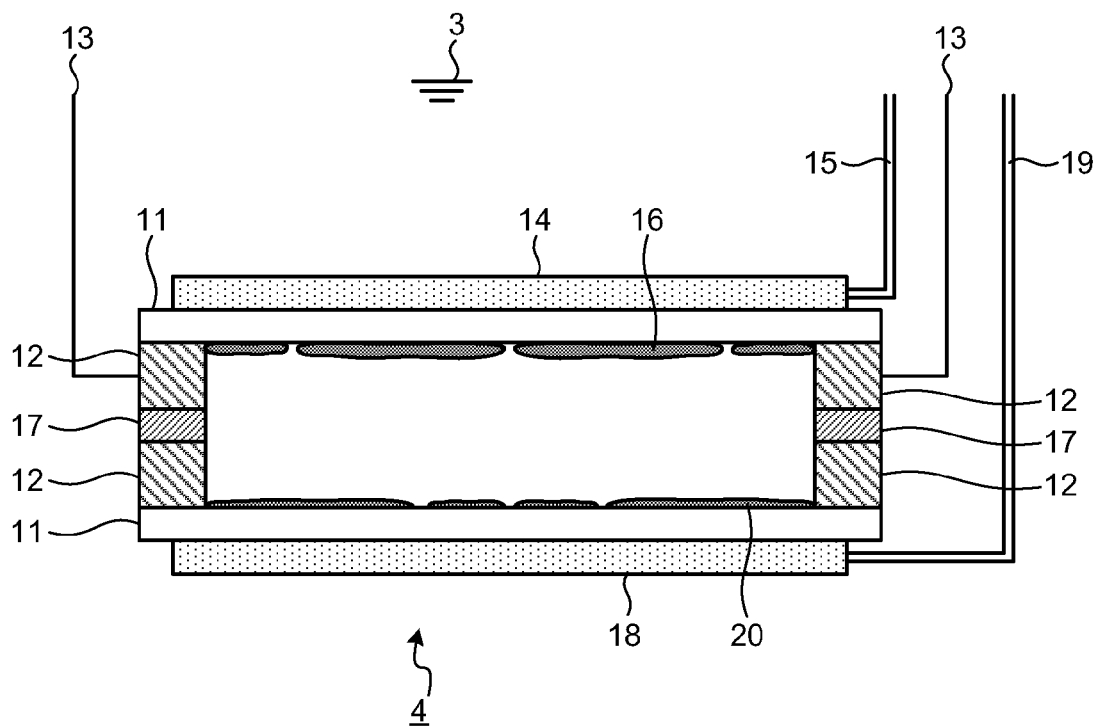
FIG. 6 is a detailed diagram of the structure of a detection member according to a third embodiment.

FIG. 6 is a diagram of the detailed structure of a detection member according to a third embodiment. The structural components that are the same as those of FIGS. 1 and 2 are given the same reference numerals. According to the present embodiment, two plate-like pressboards 11 are arranged parallel to and opposed to each other, and two electrodes 12 are arranged at the both ends of the opposing surface of each pressboard. The detection member 4 is configured by interposing insulators 17 between the electrodes 12 arranged on one pressboard 11 and the electrodes 12 on the other pressboard 11. In other words, the two pressboards 11 share the electrodes 12 in FIG. 5, but according to the present embodiment, a pair of electrodes 12 are provided on each of the two pressboards 11 and the insulators 17 are interposed therebetween to insulate the upper and lower pressboards 11 from each other so that the surface resistance between each pair of electrodes 12 can be independently detected. In the same manner as in the first embodiment, the surface resistance measurement lead 13 is connected to the electrodes 12 deposited on the pressboard 11. For the sake of simplicity of the drawing, the surface resistance measurement lead 13 connected to the electrodes 12 on the lower pressboard 11 is omitted.

The heater 14 is arranged in contact with one pressboard 11 on the surface of the pressboard 11 that is not the opposing surface. Furthermore, a heater 18 is arranged in contact with the other pressboard 11 on the surface of the pressboard 11 that is not the opposing surface. The heater lead 15 is connected to the heater 14, while a heater lead 19 is connected to the heater 18. Because the level of heating of the heater 14 and the heater 18 can be independently controlled by the heater controlling device 8, the two pressboards 11 can be set at different temperatures. These temperatures should both be set higher than the temperature of the coil unit. In this example, because the temperature of the lower pressboard 11 is set lower than that of the upper one, the amount of copper sulfide 20 precipitated on the lower pressboard 11 is smaller than the amount of copper sulfide 20 precipitated on the upper pressboard 11.

In a transformer installed in a core electric power system, even when an abnormality is found, maintenance work may not be easily conducted. For such an apparatus, the abnormality in the apparatus should be detected as soon as possible, and at the same time, the state of progress of the abnormality should be monitored.

The detection member 4 according to the embodiment of FIG. 6 can be applied to such a transformer. In the detection member 4 that is incorporated, its surface resistance is lowered more quickly than in the surface resistance detection member 4 illustrated in FIG. 2. According to the present embodiment, there is enough copper sulfide precipitated on the upper pressboard 11 that is brought to a high temperature to lower the surface resistance. However, because the temperature of the lower pressboard 11 is low, an electrical path is not formed even though there is some copper sulfide precipitated on the pressboard 11. Thus, there is a relatively long period of time between the detection of apparatus abnormality in the upper pressboard 11 and an actual failure caused in the apparatus, and therefore the maintenance work can be prepared during this time period. The normal operation of the apparatus can be maintained until reduction in the surface resistance is detected on the lower pressboard 11. Thus, systematic maintenance can be offered.

The present embodiment is not limited to the above structure, but the same effect as in the present embodiment can be obtained by incorporating multiple solid insulators to have multiple detection surfaces and setting the solid insulators at different temperatures. However, with the structure of the present embodiment, the size of the detection member 4 can be made compact.

INDUSTRIAL APPLICABILITY

The present invention is applicable to an oil immersed electrical apparatus such as a transformer in which a copper coil covered with insulating paper is arranged in insulating oil.

The invention claimed is:

1. An oil immersed electrical apparatus, in which an electrical apparatus main body is housed in a container filled with insulating oil and the electrical apparatus main body includes a current carrying medium whose surface is covered by an insulating member, comprising:
a solid insulator that is prepared with a same material as the insulating member and has two electrodes on a surface, and a heater arranged on another surface of the solid insulator, the solid insulator being adopted as a detection member that is arranged in contact with the insulating oil to detect a change in an insulation resistance between the electrodes.

2. The oil immersed electrical apparatus according to claim 1, wherein the solid insulator is shaped into a plate, the two electrodes are arranged on one surface of the solid insulator.

3. The oil immersed electrical apparatus according to claim 2, wherein a temperature of the detection member is set higher than a temperature of the current carrying medium by the heater.

4. The oil immersed electrical apparatus according to claim 3, wherein a heating area of the heater is greater than a distance between the electrodes.

5. The oil immersed electrical apparatus according to claim 3, wherein the detection member is arranged in an upper portion of the container.

6. The oil immersed electrical apparatus according to claim 3, wherein the detection member comprises a plurality of the solid insulators.

7. The oil immersed electrical apparatus according to claim 6, wherein the detection member comprises a pair of plate-like solid insulators that are arranged opposed to each other and the two electrodes sandwiched between the pair of solid insulators.

8. The oil immersed electrical apparatus according to claim 2, wherein a heating area of the heater is greater than a distance between the electrodes.

9. The oil immersed electrical apparatus according to claim 8, wherein the detection member is arranged in an upper portion of the container.

10. The oil immersed electrical apparatus according to claim 8, wherein the detection member comprises a plurality of the solid insulators.

11. The oil immersed electrical apparatus according to claim 8, wherein the detection member comprises a plurality of the solid insulators, and temperatures of the solid insulators are set higher than a temperature of the current carrying medium, and set at different temperatures.

12. The oil immersed electrical apparatus according to claim 2, wherein the current carrying medium is a coil, and the insulating member is insulating paper wound around the coil.

13. The oil immersed electrical apparatus according to claim 12, wherein the coil is a copper coil.

14. The oil immersed electrical apparatus according to claim 13, wherein the solid insulator is prepared with cellulose.

15. The oil immersed electrical apparatus according to claim 2, wherein the solid insulator is formed by a pressboard.

16. The oil immersed electrical apparatus according to claim 2, wherein the detection member is arranged in an upper portion of the container.

17. The oil immersed electrical apparatus according to claim 2, wherein the detection member comprises a plurality of the solid insulators.

18. The oil immersed electrical apparatus according to claim 17, wherein the detection member comprises a pair of plate-like solid insulators that are arranged opposed to each other and the two electrodes sandwiched between the pair of solid insulators.

19. The oil immersed electrical apparatus according to claim 2, wherein the detection member comprises a plurality of the solid insulators, and temperatures of the solid insulators are set higher than a temperature of the current carrying medium, and set at different temperatures.

20. The oil immersed electrical apparatus according to claim 19, wherein the detection member comprises a pair of plate-like solid insulators that are arranged opposed to each other, the electrodes arranged on opposing surfaces of the solid insulators, and insulating members arranged between the electrodes deposited on one of the solid insulators and the electrodes deposited on the other one of the solid insulators.

* * * * *